(12) United States Patent
Dennis et al.

(10) Patent No.: US 7,202,282 B2
(45) Date of Patent: Apr. 10, 2007

(54) MICROEMULSIONS FOR SELECTIVE MOLECULAR SEPARATION

(75) Inventors: Donn M. Dennis, Gainesville, FL (US); Timothy E. Morey, Gainesville, FL (US); Richard E. Partch, Hannawa Falls, NY (US); Dinesh O. Shah, Gainesville, FL (US); Manoj Varshney, Gainesville, FL (US)

(73) Assignee: University of Florida, Gainesville, FL (US)

( * ) Notice: Subject to any disclaimer, the term of this patent is extended or adjusted under 35 U.S.C. 154(b) by 233 days.

(21) Appl. No.: 10/420,608

(22) Filed: Apr. 22, 2003

(65) Prior Publication Data

US 2004/0011644 A1    Jan. 22, 2004

Related U.S. Application Data

(60) Provisional application No. 60/375,281, filed on Apr. 22, 2002.

(51) Int. Cl.
*B01F 3/08* (2006.01)
*A01N 43/40* (2006.01)
*A61K 31/445* (2006.01)

(52) U.S. Cl. .................. 516/53; 210/643; 514/330
(58) Field of Classification Search .................. 516/53; 210/643; 514/330
See application file for complete search history.

(56) References Cited

U.S. PATENT DOCUMENTS 4,337,225 A * 6/1982 Dines ..................... 210/638
4,587,106 A * 5/1986 Bauer et al. ............... 210/643
5,612,300 A * 3/1997 von Blucher et al. ......... 516/58

OTHER PUBLICATIONS

Drew Myers, Surfactant Science and Technology, second edition (VCH Publishers, NY, NY, copyright 1992) pp. 153-155, 7-1994.*
Leon M. Prince, Microemulsions Theory and Practice, Acedemic Press, Inc, NY, NY (copyright 1977) (01-1979), pp. 68-71.*
Altria, K.D. "Background Theory and Applications of Microemulsion Electrokinetic Chromatography" *Journal of Chromatagraphy*, 2000, pp. 171-186, vol. 892, month unknown.
Altria, K.D. "Application of Microemulsion Electrokinetic Chromatography to the Analysis of a Wide Range of Pharmaceuticals and Excipients" *Journal of Chromatography*, 1999, pp. 371-386, vol. 844, month unknown.
Fu, X. et al. "Microemulsion Electrokinetic Chromatographic Separation of Antipyretic Analgesic Ingredients" *Journal of Chromatography*, 1996, pp. 353-356, vol. 735, month unknown.
Debusschere, L. et al. "Separation of Cardiac Glycosides by Micellar Electrokinetic Chromatography and Microemulsion Electrokinetic Chromatography" *Journal of Chromatography*, 1997, pp. 227-233, vol. 779, month unknown.
Nishi, H. "Pharmaceutical Applications of Micelles in Chromatography and Electrophoresis" *Journal of Chromatography*, 1997, pp. 243-264, vol. 780, month unknown.
Nishi, H. and Terabe, S. "Micellar Electrokinetic Chromatography Perspectives in Drug Analysis" *Journal of Chromatography*, 1996, pp. 3-27, vol. 735, month unknown.

(Continued)

*Primary Examiner*—Daniel S. Metzmaier
(74) *Attorney, Agent, or Firm*—Saliwanchik, Lloyd & Saliwanchik

(57) ABSTRACT

The subject invention provides microemulsions having, as one component thereof, electron-deficient aromatic rings, e.g.. di(trifluoromethyl) benzene, for efficient separation and/or isolation of target molecules, e.g., bupivacaine.

4 Claims, 2 Drawing Sheets

OTHER PUBLICATIONS

Vomastova, L. et al. "Microemulsion and Micellar Electrokinetic Chromatography of Steroids" *Journal of Chromatography*, 1996, pp. 107-113, vol. 681, month unknown.

Watarai, H. "Microemulsions in Separation Sciences" *Journal of Chromatography*, 1997, pp. 93-102, vol. 780, month unknown.

* cited by examiner

Cocaine

Bupivacaine

Microemulsion

Smart Microemulsion

US 7,202,282 B2

MICROEMULSIONS FOR SELECTIVE MOLECULAR SEPARATION

CROSS-REFERENCE TO A RELATED APPLICATION

This application claims the benefit of provisional patent application Ser. No. 60/375,281, filed Apr. 22, 2002, which is hereby incorporated by reference in its entirety.

GOVERNMENT SUPPORT

This invention was made with government support under a grant awarded from the National Science Foundation under ERC Grant Number EEC 9402989. The government has certain rights in the invention.

BACKGROUND OF INVENTION

In many fields it is often necessary to separate different entities at the molecular level. The efficiency of such separations, or even the ability to make the separations at all, is often a determining factor in the feasibility of a particular product or method. Particularly at the industrial scale, there is a need for new and improved processes which facilitate separation, at the molecular level, of closely related molecules in a bulk medium.

A microemulsion is a thermodynamically stable dispersion of one liquid phase into another, stabilized by an interfacial film of surfactant. Microemulsions are typically clear solutions, as the droplet diameter is approximately 100 nanometers or less. The interfacial tension between the two phases is extremely low.

Microemulsions are distinct from (macro)emulsions, which are thermodynamically unstable dispersions of macroscopic droplets of one or more liquid and/or liquid crystalline phases in a continuous liquid. However, a microemulsion may be one of the phases of an emulsion. The microemulsion may appear as one of three phases, for example, a middle phase in simultaneous equilibrium with a top or upper oleic phase, and a bottom or lower aqueous phase. Because the three phases are close to a tricritical point (where all three phases simultaneously become a single phase), the interfacial tensions among the three phases are several orders of magnitude less than the tensions produced by conventional micellar solutions. Moreover, by suitable changes of temperature, salinity, or other compositional variable, the composition of the middle phase can be made to vary continuously between that of the bottom and top phases.

Microemulsions may be oil-in-water, water-in-oil, or bicontinous states of matter characterized by isotropic composition, thermodynamic stability, submicron particle dimension, and transparency. Typically, the elements include an oil, a surfactant (e.g., ionic, nonionic, or both), and a cosurfactant mixed into a bulk media (e.g., water, saline). Because the core of a microemulsion can be be oil, these microemulsions may be useful for molecular separation of hydrophobic molecules from a bulk solution of an aqueous nature into the oil core of each microemulsion nanoparticle. However, because hydrophobic forces nonspecifically apply to all lipophilic molecules, such microemulsions will also partition nontargeted molecules. For example, whereas a microemulsion may sequester a toxic agent from blood, it may also remove other lipophilic agents that are either native (e.g., steroids) or foreign (e.g., injected drugs) and that may be beneficial.

Currently, no way exists to preclude unintended removal of these non-targeted molecules. Thus, these microemulsions cannot distinguish targeted and nontargeted molecules for separation from bulk media. Therefore, a need exists for improved methods for molecular separation.

BRIEF SUMMARY

The subject invention provides unique materials and methods for selectively removing one type of molecule from a medium while leaving other types of molecules in the medium. The subject invention enables selective separation of molecules from a medium using forces unrelated to hydrophic forces, which nonspecifically apply to all lipophilic molecules. In a preferred embodiment of the subject invention, microemulsions are specifically designed to facilitate effective separation of even closely related chemical entities.

Specifically exemplified herein are microemulsions that are designed to have either electron-deficient structures or electron-rich structures in order to drive the separation process. By modifying the electron densities of the microemulsions it is possible according to the subject invention to separate compounds having different electron densities.

The systems of the subject invention can be used to separate contaminants from a bulk material. Alternatively, systems of the subject invention can be designed to isolate even trace amounts of a desired product from bulk media.

The materials and methods of the subject invention are applicable in a wide variety of settings. For example, the separation technology of the subject application can be of benefit for multiple processes including, chemical, oil, cosmetic, pharmaceutical, agricultural, and military.

In a specific embodiment, the microemulsions of the subject invention can be used for nerve gas detoxification purposes in vivo or ex vivo. In another embodiment, the pharmaceutical industry can use the materials and methods of the subject invention to extract lipophilic compounds. The primary benefit is to add an additional technique for molecular separations.

DETAILED DISCLOSURE

Figure 1A:
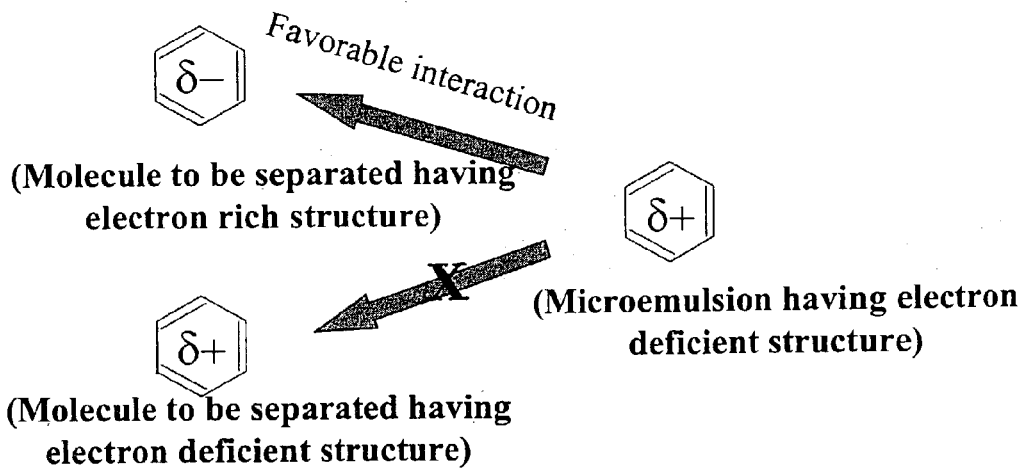
FIGS. 1A and 1B show the presence or absence electron interactions to facilitate molecular separation.

The subject invention provides unique materials and methods for selectively removing molecules from a medium. In a preferred embodiment of the subject invention, microemulsions are specifically designed to facilitate effective separation of even closely related chemical entities.

The subject invention provides materials and methods for selectively removing molecules from a medium using forces unrelated to hydrophobic forces, which nonspecifically apply to all lipophilic molecules. Specifically exemplified herein are microemulsions that are designed to have either electron-deficient structures or electron-rich structures in order to drive the separation process. By modifying the electron densities of the microemulsions it is possible according to the subject invention to separate compounds having different electron densities.

The novel features of the subject invention include:
1. For the first time, microemulsions are functionalized for selective separation of molecules from a bulk medium.
2. Microemulsions are designed based on electron acceptor or electron donating properties of the dispersing components of the microemulsion.
3. The microemulsions of the subject invention are advantageous due to their stability compared to macroemulsions.
4. The microemulsions can be prepared even in water having inorganic ions.
5. The subject invention provides a highly cost effective, simple, and efficient separation process.
6. The subject invention provides a novel way of dispersing or extracting molecules for direct applications or for incorporation in various formulations.
7. The subject invention enables separation or extraction of molecules wherein the tiny particles enable better coverage of a larger area.

One definition of a microemulsion is: an oil-in-water emulsion with a particle size below visible light scattering and which is physically stable. To the naked eye, a perfect microemulsion is indistinguishable from an aqueous solution. Microemulsions typically contain a surfactant and/or other amphiphile(s); one or more nonpolar components, such as hydrocarbons; water; and, frequently, inorganic salt(s). The surfactant(s) may be nonionic, ionic, or amphoteric; but most ionic surfactants also require a nonionic cosurfactant or amphiphile to suppress formation of liquid crystals.

In a preferred embodiment, the method of the subject invention involves utilizing an additional force in the microemulsion system that attracts the targeted molecule while having either no effect on, or repels, non-targeted molecules. In one embodiment, the oil is of a singular nature that is chosen specifically to attract the targeted molecule using both hydrophobic forces and a new, unique force. Subsequently, a microemulsion is synthesized from this oil. In another embodiment, molecules that are added to a conventional oil specifically attract the targeted molecule with minimal-to-no effect on molecules not targeted for separation. Advantageously, these novel microemulsions can selectively distinguish between targeted and nontargeted molecules for separation.

One embodiment of the subject invention provides a microemulsion concentrate that can be diluted or mixed with water, saline or hard water, to instantaneously form an oil-in-water microemulsion.

Following is an example that illustrates procedures for practicing the invention. These examples should not be construed as limiting. All percentages are by weight and all solvent mixture proportions are by volume unless otherwise noted

EXAMPLE 1

Figure 1B:
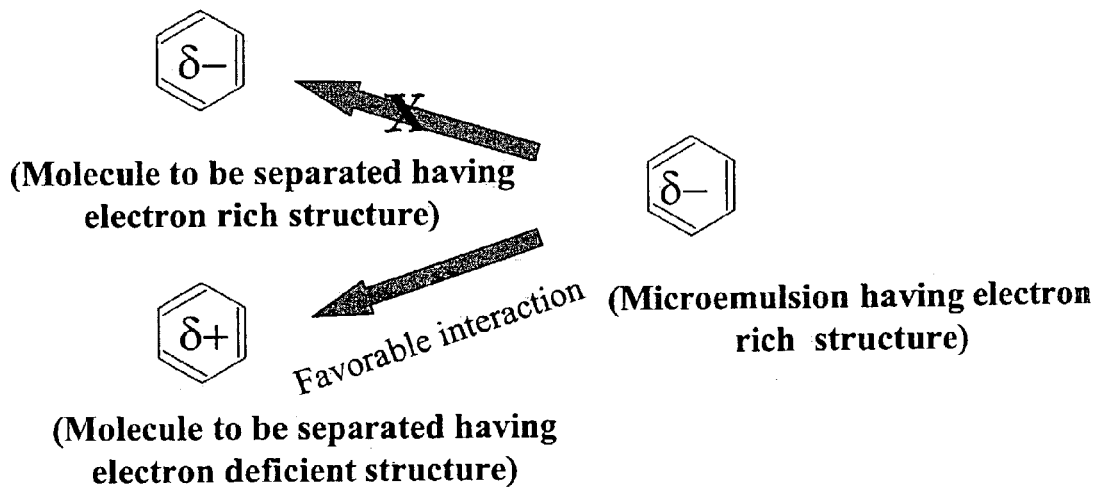
Figure 2A:
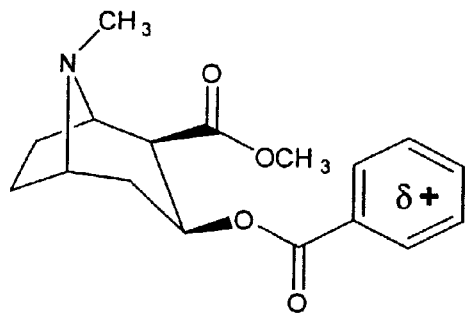
FIGS. 2A and 2B show two, commonly used local anesthetic molecules: cocaine (panel A) and bupivacaine (panel B).
Figure 2B:
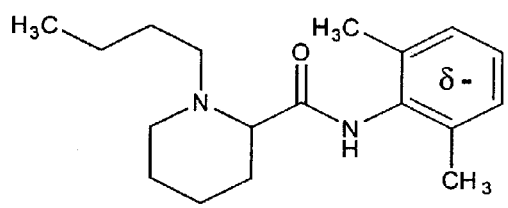
Figure 3:
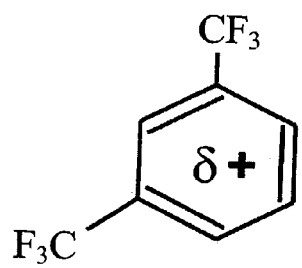
FIG. 3 shows molecular structure of 1,3 di(trifluoromethyl) benzene.
Figure 4A:
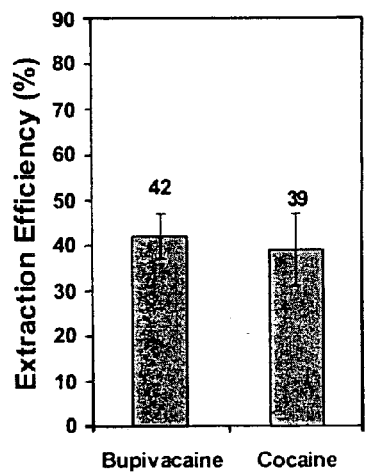
FIGS. 4A and 4B show the molecular separation achieved using the method of the subject invention.
Figure 4B:
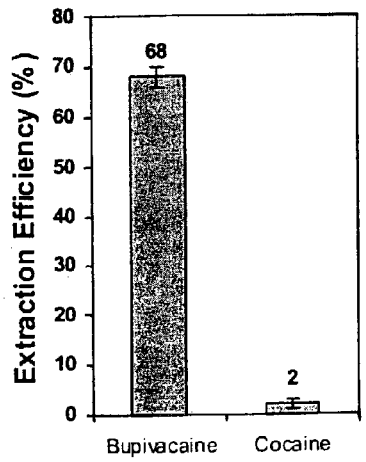

In one embodiment, the materials and/or methods of the subject invention can be used to separate drugs of the same class. A specific embodiment involves separating local anesthetics. As shown in FIG. 1, a microemulsion having an electron deficient aromatic ring strongly attracts a molecule that has an electron-rich aromatic ring or vice-versa due to the presence of π-π interactions. This is accomplished by exploiting differences in electron density in π electron orbitals.

In a specific embodiment, as illustrated in FIG. 2, differences in electron density in the π electron orbitals of the benzene rings of local anesthetic molecules, bupivacaine and cocaine, are used to selectively separate the two molecules. In these molecules, the π electron orbitals are aligned at right angles to the planar surface of the benzene rings. Differences in substitution by the side chain in cocaine or bupivacaine cause either electron depletion ($\delta^+$) or enrichment ($\delta^-$). Such characteristics can be used to selectively separate these molecules.

According to the subject invention, any oil or "mating" molecule with a benzene ring is acceptable in providing a microemulsion system, as long as the substitutions are electron withdrawing from the benzene ring into the side chains. In this case, the electron deficient ring is a component of a molecule (e.g., 1,3 di(trifluoromethyl) benzene) that, at room and physiological temperatures, is an oil (FIG. 3). Thus, these oil molecules can be used to construct the lipid core of a microemulsion or may be added as solutes into the lipid core of a microemulsion wherein another oil serves as the lipid core.

FIG. 4 shows that the method of the subject invention can be used to selectively partition bupivacaine, but not cocaine.

In addition, selection of surfactant or cosurfacant with appropriate electron properties can cause selective molecular separations.

It should be understood that the examples and embodiments described herein are for illustrative purposes only and that various modifications or changes in light thereof will be suggested to persons skilled in the art and are to be included within the spirit and purview of this application.

We claim:

1. An oil-in-water microemulsion comprising a surfactant and, optionally, a co-surfactant wherein said microemulsion has at least one component that creates a force, wherein said force attracts a target molecule while having either no effect on, or repels, non-target molecules, such that target molecules earl be separated from non-target molecules, wherein said force results from a molecule comprising an electron-deficient aromatic ring wherein said electron-deficient aromatic ring is a benzene ring to which is attached one or more electron withdrawing side chains, wherein at least one electron withdrawing trifluoromethyl side chain is present on said benzene ring.

2. The microemulsion, according to claim 1, wherein said molecule comprising an electron-deficient aromatic ring is a di(trifluoromethyi) benzene.

3. The rnicroemulsion, according to claim 1, comprising 1,3 di(trifluoromethyl) benzene.

4. The microemulsion, according to claim 3, wherein the target molecule is bupivacaine.

* * * * *